United States Patent [19]
Simon et al.

[11] Patent Number: 5,968,007
[45] Date of Patent: Oct. 19, 1999

[54] POWER-LIMIT CONTROL FOR ULTRASONIC SURGICAL INSTRUMENT

[75] Inventors: William P. Simon, New Milford, Conn.; Alan Broadwin, Larchmont, N.Y.; John Massa, Danbury, Conn.

[73] Assignee: Sonics & Materials, Inc., Newtown, Conn.

[21] Appl. No.: 08/848,918

[22] Filed: May 1, 1997

[51] Int. Cl.⁶ .................................................. A61B 17/20
[52] U.S. Cl. .......................................................... 604/22
[58] Field of Search ................. 604/22; 606/32, 606/33–42, 45, 167, 169; 607/100, 101, 102, 115

[56] References Cited

U.S. PATENT DOCUMENTS

| | | | |
|---|---|---|---|
| 3,980,906 | 9/1976 | Kuris et al. ................................ | 601/2 |
| 5,299,175 | 3/1994 | Gallego-Juarez et al. .............. | 367/138 |
| 5,655,956 | 8/1997 | Ferreira et al. .......................... | 451/165 |

*Primary Examiner*—Manuel Mendez
*Attorney, Agent, or Firm*—St. Onge Steward Johnston & Reens LLC

[57] ABSTRACT

A control for an ultrasonic surgical instrument is described wherein a transducer having an elongate tip is vibrated to perform surgery. The amplitude of the vibrations by the tip are controlled and the power delivered to the tip can be set so that the operator of the instrument can in effect render the instrument sensitive to different tissues to avoid damage thereto and enhance the safety of the patient.

12 Claims, 2 Drawing Sheets

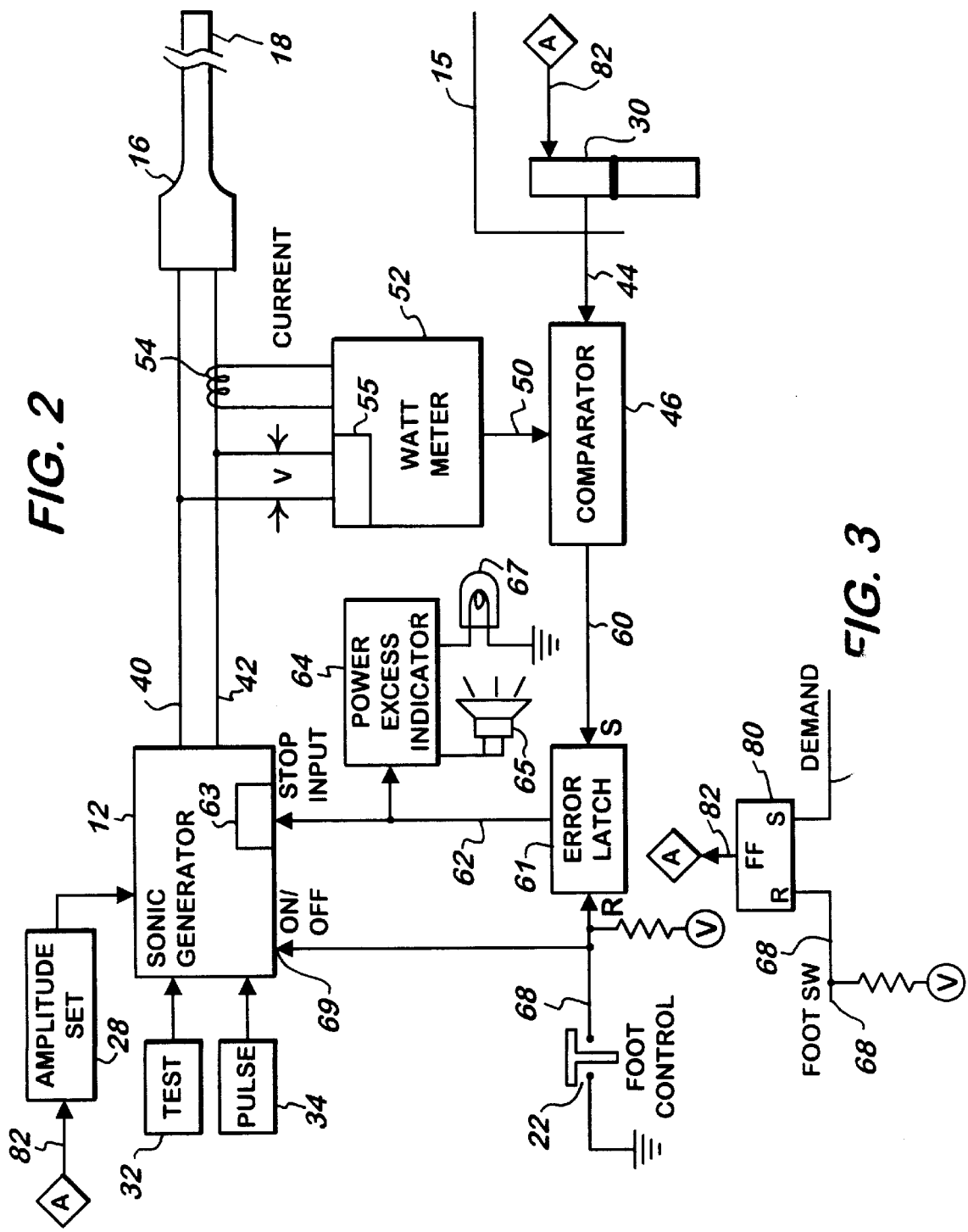

5,968,007

POWER-LIMIT CONTROL FOR ULTRASONIC SURGICAL INSTRUMENT

FIELD OF THE INVENTION

This invention generally relates to a method and apparatus for operating an ultrasonic surgical instrument and more specifically to an apparatus for providing an ultrasonic surgical instrument whose sensitivity to different body tissues can be selected.

BACKGROUND OF THE INVENTION

Ultrasonic surgical instruments have been available since the early 1970's. One early example is the Cavitron Phaco-Emulsifier, a Cavitron trademark, which provided an apparatus for eye surgery without tip vibration amplitude control. The vibration tip amplitudes were low and the load reflected back to the handpiece during surgery was a small percentage of the total power provided by the power supply used in the apparatus.

With the arrival of the Cavitron Ultrasonic Surgical Aspirator in 1976, the surgical tip amplitude was increased some five fold and the electrical power to drive the tip was approximately doubled. In addition, the tip amplitude was controlled so that it could remain constant for the full power range available from the power supply in the apparatus. This yielded an effective ultrasonic surgical instrument which was powerful enough to fragment and remove a broad range of tissues, from very soft parenchymal tissue to more fibrous and elastic membranes.

The surgeon was then faced with a dilemma. For most effective operation of the ultrasonic instrument, the amplitude of vibration needed to be near the maximum available. However, at high amplitude settings, the selectivity of tissue removal, i.e. the ability of the instrument to discriminate between high and low water content tissues, was diminished. As a result, the ultrasonic surgical instrument easily fragmented tissue that the surgeon wanted to remove but also fragmented tissue that was not intended to be removed.

One solution to this problem is proposed by U.S. Pat. No. 4,827,911. In this patent an ultrasonic surgical instrument is described wherein the ultrasonic tip is activated in a pulsed manner. This reduces the average energy into the tissue while providing a high amplitude tip motion for effective tissue fragmentation.

However, in recent years slender surgical tips started to be made available. Such tips are advantageous for many minimal invasive procedures. To counteract the significant loads presented to the power supplies used in the ultrasonic instruments and employing the slender tips, manufacturers have increased the maximum available power so that the ultrasonic tips will not stall or worse, have a reduced amplitude, which slows down the surgical procedure, increases the frictional heat transmitted to the patient, and heats the tip so that its functional life is reduced.

Hence, increasing the maximum available power does not come without problems. The increased available power, independent of the desired tip amplitude, decreases the sensitivity of the surgical instrument and can result in unwanted damage to surrounding tissue, perforation of tissue in front of the tip and reduced protection to the patient.

SUMMARY OF THE INVENTION

With an ultrasonic surgical instrument in accordance with the invention an enhanced instrument sensitivity is achieved for the benefit of the surgeon who can select, in addition to the desired tip amplitude, the maximum power that is to be made available for any particular tip amplitude level. As a result the surgeon, after selecting the amplitude, can control the available reserve power to an expected needed level. Hence, if the surgeon encounters tissue which increases the load on the ultrasonic tip beyond the selected power level, the instrument shuts down and a visible and/or audible alarm is given to the surgeon.

One aspect of the invention, therefore, involves an apparatus with which the surgeon can carefully approach a delicate tissue to be ultrasonically fragmented with just the right amount of maximum useable power. If, thereupon, an excessive load is encountered so that the tip's ultrasonic amplitude level would or might drop, the tendency of the electrical power circuit to compensate with additional power is avoided by the set point power limit provided by this invention. The power set point can in such case be used to change the output power such as by shutting down the instrument. When an excessive load causes the instrument to shut down a release of a control, such as a foot switch, can reset the system, which restarts when the switch is again depressed. As a result the surgeon can operate near sensitive structures with increased safety to the patient.

It is, therefore, an object of the invention to provide an ultrasonic surgical instrument that can be more safely and accurately matched to the requirements of the surgical procedure so that in effect a tissue selective control is obtained. It is a further object of the invention to provide an ultrasonic surgical instrument with which operation of a vibrating surgical tip can be done next to sensitive tissue structures with increased safety to the patient and a decreased chance of an undesired perforation or other damage to surrounding tissue. It is still further an object of the invention to provide an ultrasonic surgical instrument with which the instrument can be adjusted to meet surgical conditions in a user friendly manner.

These and other advantages and objects of the invention can be understood from the following description of a preferred embodiment as shown in the drawings.

BRIEF DESCRIPTION OF DRAWINGS

FIG. 2 is a block diagram for a control of the instrument of FIG. 1; and

FIG. 3 is a block diagram of an alternate control for governing the power output from the ultrasonic generator in an ultrasonic surgical instrument in accordance with the invention.

DETAILED DESCRIPTION OF DRAWINGS

Figure 1:
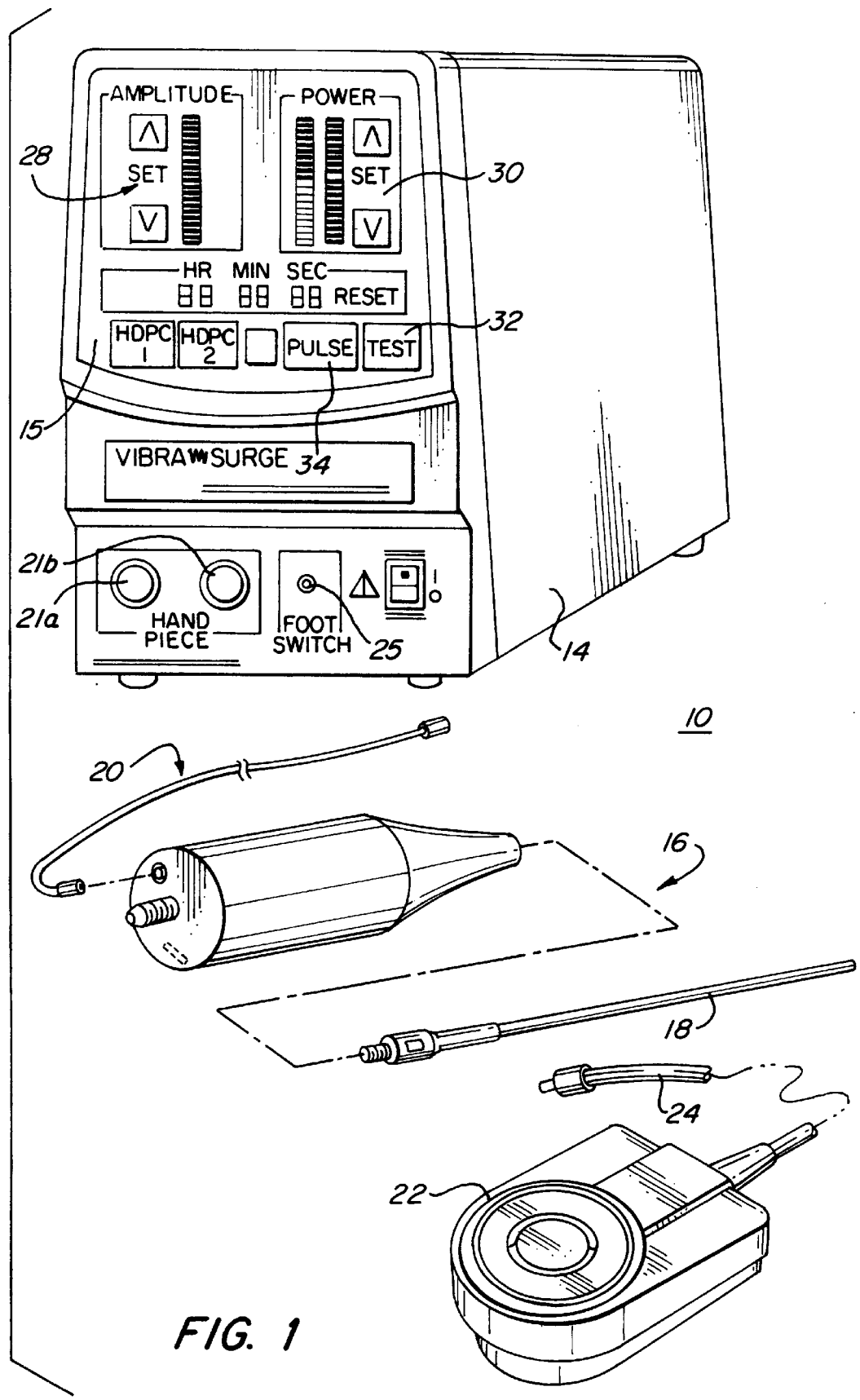
FIG. 1 is a perspective view of an ultrasonic surgical instrument in accordance with the invention.

With reference to FIGS. 1 and 2 an ultrasonic instrument 10 in accordance with the invention is shown. The instrument includes a sonic generator 12 in a housing 14 having a front panel 15 and an ultrasonic surgical transducer 16 having a long slender tip 18. Other tips 18 can be used and tip 18 is shown here for illustrative purposes. The transducer is connected to the sonic generator 12 by a high voltage cable 20 through a connector 21a or 21b in the front panel 15. The activation of instrument 10 is controlled with a control such as a foot switch 22 also connected to sonic generator 12 by a cable 24 that fits in a connector 25 in the front panel 15.

The sonic generator is of a standard type and includes a power supply and frequency source as are well known in the art. The front panel 15 of the housing 14 is provided with controls for the sonic generator 12 such as an amplitude selector 28 and a power selector 30 and various mode controls for testing at 32, and for a pulse mode at 34. The pulse mode would cause ultrasonic impulses from the tip 18 varying from full on to fully off in a manner as is well known in the art.

The sonic generator 12 delivers high frequency power to ultrasonic transducer 16 via power lines 40, 42 in cable 20. The voltage level applied across lines 40, 42 as controlled by amplitude selector 28 determines the amplitude of the ultrasonic vibrations at the end of tip 18. It should be understood, however that, depending upon the type of transducer 16 that is being used, the tip amplitude may be determined by varying the current delivered through the power lines 40, 42. The invention is, therefore, not to be limited to a voltage amplitude control.

The ultrasonic surgical instrument is further controlled by limiting the power that can be applied to the transducer 16 to a reference level as selected by control 30. This provides a reference signal on a line 44 as indicative of the desired maximum power level to a comparator 48. This compares a signal on a line 50, indicative of the power being delivered to the transducer 16, with the signal of the selected power set point on line 44. The signal on line 50 can be the actual power delivered to the transducer 16 as determined by a watt meter 52 having a current sensor 54 coupled to one of the power lines 40 or 42 and a voltage sensor 55 inside the watt meter 52.

The signal indicative of the power being delivered to ultrasonic transducer 16 need not be the actually computed watts. For example, if the voltage level to the transducer remains essentially fixed for a correspondingly fixed amplitude level, then a signal indicative of the power output can be determined by sensing the current only. Or, if the transducer is of a type wherein the amplitude is determined by the current level and if this is to be at a constant level, then a signal indicative of the output power can be obtained by monitoring the voltage across lines 40, 42. The use herein of terminology indicating the output power to an ultrasonic surgical transducer thus includes the various available techniques for obtaining such signal.

Hence, once the comparator 46 measures that the output power exceeds the desired set point level as determined by the signal on line 44, an output demand signal is produced on line 60. This demand signal is applied to an appropriate error latch 61 whose ouput on line 62 is applied to a gate or switch 63 inside the sonic generator 12 and in the embodiment causes it to shut down. Such shut down can be achieved by inhibiting the application of an oscillator used to generate the ultrasonic signal or with the use of a semiconductor power switch or in the same manner as the release of the foot switch 22 causes the cessation of ultrasonic power. Alternatively the response to the demand signal can be a reduction of power or, without a change in the ouput power, merely the generation of either an audible or visual alarm to the surgeon.

The occurrence of an excess power demand condition is indicated to the operator of the ultrasonic surgical instrument 10 by activating a suitable alarm indicator 64 for as long as the excess power demand condition exists or for a preset time. The alarm indication can be visual by way of a light 65 and/or audible by way of a speaker 67. The error signal indication from comparator 46 could also be used to reduce the output amplitude from the sonic generator 12 with a circuit as shown in FIG. 3.

The interruption and control of power to the surgical instrument can continue to be achieved with the foot switch 22 by applying the signal on line 68 from foot switch 22 to its regular on/off control input 69 on the sonic generator 12 while also applying the foot control signal on that line to the reset input of error latch 61.

A reduction of ultrasonic output power or tip vibration amplitude can be achieved with a suitable amplifier control responsive to the demand signal on line 60 from the comparator 46. The reduction of output power may also be accompanied by a reduction in tip amplitude, in which case the occurrence of either a visual or audible alarm will alert the surgeon of this condition so that he or she can take appropriate action.

If a desired response to the excess power demand signal on line 60 is a reduction of output tip vibration amplitude, this can be done by applying a latch signal to the appropriate control. In such case, as shown in FIG. 3, the demand signal on line 60 causes a setting of a flip flop 80. The output 82 of the flip flop 80 is applied to the amplitude set point control 28 to cause it to change, resulting in a reduction of desired amplitude level. A similar alteration of the output power can be achieved by applying the signal on line 82 to the power set point control 30.

With the use of a power governor applied to the sonic generator 12 a surgeon using the ultrasonic generator can apply fine control over the ultrasonic surgical instrument. Adipose tissue near a critical artery can be more safely removed at a power setting sufficient to fragment the adipose tissue but not sufficient to do damage to the artery wall whose nearby presence could increase the load on the tip's amplitude and thus result in an otherwise automatic increase in power level. This condition is avoided by limiting the power to what is just needed for the particular procedure.

Having thus explained a preferred embodiment in accordance with the invention its advantages can be appreciated. Variations from the illustrated embodiment can be made without departing from the scope of the invention as determined by the following claims.

What is claimed is:

1. An apparatus for limiting the ultrasonic power from an ultrasonic surgical instrument having an ultrasonic transducer with a tip whose vibration amplitude is controlled by an output parameter of a sonic generator for driving the transducer, comprising:

means for producing a power signal indicative of the ultrasonic output power delivered to the ultrasonic transducer;

means for generating a reference signal representative of the desired output power to the ultrasonic transducer;

means responsive to the power signal and the reference signal for generating a demand signal when the output power to the ultrasonic transducer exceeds the desired output power; and means for using the demand signal.

2. The apparatus as claimed in claim 1 wherein said power signal producing means comprises means for sensing the current flowing to the ultrasonic transducer.

3. The apparatus as claimed in claim 1 wherein said power signal generating means comprises means for sensing the voltage applied to the ultrasonic transducer.

4. The apparatus as claimed in claim 1 wherein said means for using the demand signal comprises an audible alarm.

5. The apparatus as claimed in claim 1 wherein said means for using the demand signal comprises a visual indication.

6. The apparatus as claimed in claim 1 and further including means responsive to said demand signal for changing the output power to said ultrasonic transducer.

7. The apparatus as claimed in claim 6 wherein said output power changing means comprises a switch actuated by said demand signal and interposed to effectively cause an interruption of ultrasonic power to said ultrasonic transducer.

8. An apparatus for limiting the ultrasonic power from an ultrasonic surgical instrument having an ultrasonic transducer with a tip whose vibration amplitude is controlled by an output parameter of a sonic generator for driving the transducer, comprising:

means for producing a power signal indicative of the ultrasonic output power delivered to the ultrasonic transducer;

means for generating a reference signal representative of the desired output power to the ultrasonic transducer;

means responsive to the power signal and the reference signal for generating a demand signal when the output power to the ultrasonic transducer exceeds the desired output power;

means responsive to the demand signal for reducing the output power from the sonic generator; and means responsive to said demand signal for providing an indication thereof.

9. The apparatus as claimed in claim 8 wherein said indication providing means comprises an audible alarm.

10. The apparatus as claimed in claim 8 wherein said means for reducing the output power interrupts the output power without reducing the tip vibration amplitude.

11. An apparatus for limiting the ultrasonic power from an ultrasonic surgical instrument having an ultrasonic transducer with a tip whose vibration amplitude is controlled by an output parameter of a sonic generator for driving the transducer, comprising:

means for producing a power signal indicative of the ultrasonic output power delivered to the ultrasonic transducer;

means for generating a reference signal representative of the desired output power to the ultrasonic transducer;

means responsive to the power signal and the reference signal for generating a demand signal when the output power to the ultrasonic transducer exceeds the desired output power;

a foot switch coupled to generate a signal to activate the sonic generator; and means responsive to the demand signal and the signal generated by the foot switch for interrupting the output power from the sonic generator and enabling the sonic generator after a subsequent reactivation of the foot switch.

12. A method for using an ultrasonic surgical instrument comprising the steps of:

selecting the amplitude of ultrasonic vibrations of an ultrasonic transducer driven by the instrument;

selecting a desired maximum power level to be applied to the ultrasonic transducer;

comparing the actual power applied to the transducer to the desired maximum power level and producing a power signal indicative thereof; and interrupting the power to the ultrasonic transducer when the actual power exceeds the desired maximum power level.

* * * * *